United States Patent [19]

Line et al.

[11] Patent Number: 5,722,342
[45] Date of Patent: Mar. 3, 1998

[54] OVO ANTIBIOTIC AND MICROBIAL TREATMENT TO DIMENISH SALMONELLAE POPULATIONS IN AVIANS

[76] Inventors: J. Eric Line, 1081 Riverhaven La., Watkinsville; Norman J. Stern, 255 Gatewood Cir., Athens, both of Ga. 30607; Nelson A. Cox, 156 Valleywood Dr., Athens, Ga. 30606; J. Stan Bailey, 1290 Creekshore Dr., Athens, Ga. 30606; Catherine Ricks, 3336 Manor Ridge Dr., Raleigh, N.C. 27603; Patricia Phelps, 5208 Troutman La., Raleigh, N.C. 27613; Michael Knight, 45 Stanland Drive, Scarborough, Ontario, Canada, M1M-2G5

[21] Appl. No.: 671,743

[22] Filed: Jun. 28, 1996

[51] Int. Cl.$^6$ .................................................. A01K 45/00
[52] U.S. Cl. ........................................................ 119/6.8
[58] Field of Search ............................... 119/6.5, 6.6, 6.7, 119/6.8

[56] References Cited

U.S. PATENT DOCUMENTS

| | | |
|---|---|---|
| 2,477,752 | 8/1949 | Kiss. |
| 2,851,006 | 9/1958 | Taylor et al. . |
| 3,130,834 | 4/1964 | Goldhaft et al. . |
| 3,256,856 | 6/1966 | Nicely et al. . |
| 4,040,388 | 8/1977 | Miller et al. . |
| 4,335,107 | 6/1982 | Snoeyenbos et al. . |
| 4,458,630 | 7/1984 | Sharma et al. . |
| 4,469,047 | 9/1984 | Miller. |
| 4,593,646 | 6/1986 | Miller et al. . |
| 4,657,762 | 4/1987 | Mikkola et al. . |
| 4,681,063 | 7/1987 | Hebrank. |
| 4,903,635 | 2/1990 | Hebrank. |
| 5,056,464 | 10/1991 | Lewis. |
| 5,136,979 | 8/1992 | Paul et al. . |
| 5,176,101 | 1/1993 | Paul et al. . |
| 5,206,015 | 4/1993 | Cox et al. . |
| 5,444,045 | 8/1995 | Francis et al. . |
| 5,505,941 | 4/1996 | Paoletti. |

FOREIGN PATENT DOCUMENTS

| | | |
|---|---|---|
| 0251750 | 6/1987 | European Pat. Off. . |

OTHER PUBLICATIONS

Stern et al., "Mucosal Competitive Exclusion to Diminish Colonization of Chickens by *Campylobacter jejuni*", *Poultry Science*, vol. 73, pp. 402–407 (1994).
Stavric et al., "Undefined and Defined Bacterial Preparations for the Competitive Exclusion of Salmonella in Poultry—A Review", *J. of Food Prot.*, vol. 56(2), pp. 173–180 (1993).
Jones et al., "A Survey of *Campylobacter jejuni* Contamination in Modern Broiler Production and Processing systems", *J. of Food Prot.*, vol. 54(4), pp. 259–262 (1991).
Jones et al., "A Survey of Salmonella Contamination in Modern Broiler Production", *J. of Food Prot.*, vol. 54(7), pp. 502–507 (1991).

OOsterom et al., "Origin of Prevalence of *Campylobacter jejuni* in Poultry Processing", *J. of Food Prot.*, vol. 46(4) pp. 339–344 (1989).
Bailey et al., "Control of Salmonella and Campylobacter in Poultry Production . . . ", *Poultry Science*, vol. 72, pp. 1169–1173 (1993).
Nurmi et al., "New Aspects of Salmonella Infection in Broiler Production", *Nature*, vol. 241, pp. 210–211 (1973).
Kimmey et al., "Prevention of Further Recurrences of *Clostridium difficile* Colitis with *Saccharomyces boulardii*", *Digestive Diseases and Sciences*, vol. 35, No. 7, pp. 897–901 (1990).
Surawicz et al., "*Saccharomyces Boulardii* Prevents Recurrent C. Difficile Pseudomembranous Colitis and Diarrhea . . . " *Gastroenterology*, vol. 104(4), Part 2.
Surawicz et al., "Treatment of Recurrent *Clostridium difficile* Colitis with Vancomycin and *Saccharomyces boulardii*", *The Am. J. of Gastroenterology*, vol. 84(10) pp. 1285–1287 (1989).
Surawicz et al., "Prevention of Antibiotic–Associated Diarrhea . . . ", *Gastroenterology*, vol. 96, pp. 981–988 (1989).
Buts et al., "*Saccharomyces boulardii* for *Clostridium difficile* .. ", *J. of Ped. Gastr. and Nutr.*, vol. 16, pp. 419–425 (1993).
McFarland et al., *Saccharomyces boulardii:* "A Review of Innovative Biotherapeutic Agent", *Microbial Ecol. in Health and Disease*, vol. 6, pp. 157–171 (1993).
Blehaut et al., "Disposition Kinetics of *Saccharomyces boulardii* in Man and Rat" *Biopharmaceutics & Drug Disposition*, vol. 10, pp. 353–364 (1989).
Elmer et al., "Suppression of *Saccharomyces boulardii* . . . ", *Antimicrobial Agents and Chemotheraphy*, vol. 31(1), pp. 129–131 (1987).
Mead et al., *Letters in Applied Microbiology*, vol. 10, pp. 221–227 (1990).
Stern et al., *Avian Diseases*, vol. 32, pp. 330–334 (1988).
Sharon et al., "Carbohydrates in Cell Recognition", *Scientific American*, pp. 82–89 (Jan. 1993).
Hafez et al., "Treatment of *Salmonella enteritidis* artifically contaminated hatching eggs with pressure–differential–dipping (PDD) using antibiotics", DIALOG(R) File 50: CAB Abstracts, CAB Accession Number: 952214516.
Juven et al., "Recovery of Salmonella from Artifically . . . ", *J. of Food Prot.*, vol. 47(4), pp. 299–302 (1984).

*Primary Examiner*—Thomas Price
*Attorney, Agent, or Firm*—M. Howard Silversein; John Fado; Gail E. Poulos

[57] ABSTRACT

To reduce the level of contamination of processed poultry, pathogen-free or nearly pathogen-free birds must be delivered to the processing plant. Therefore, it is important to prevent and/or reduce early contamination and spread of Salmonella in poultry. An in ovo method of treatment with a defined microbial preparation and an antibiotic to reduce colonization of newly hatched chicks by enteropathogenic microorganisms is described.

11 Claims, No Drawings

OVO ANTIBIOTIC AND MICROBIAL TREATMENT TO DIMENISH SALMONELLAE POPULATIONS IN AVIANS

BACKGROUND OF THE INVENTION

1. Field of the Invention

The present invention relates to an in ovo treatment of avian embryos using a composition containing yeast and an antiobiotic to diminish the frequency and extent of contamination by enteropathogenic pathogens in newly hatched birds.

2. Description of Related Art

Gastrointestinal pathogens figure prominently as the principal causes of human food borne infections in many countries. Evidence supports the claim that poultry serves as an important reservoir for Salmonella in the food supply. As many as two million cases of salmonellosis occur annually in the United States (Stavric et al, Journal of Food Protection, Volume 56, No. 2, 173–180, February, 1993). The microorganisms may colonize poultry gastrointestinal tracts without any deleterious effects on the birds and, although some colonized birds can be detected, asymptomatic carriers can freely spread the microorganisms during production and processing, resulting in further contamination of both live birds and carcasses. Poultry serves as a primary reservoir for Salmonella and Campylobacter in the food supply (Jones et al., Journal of Food Protection, Volume 54, No. 7, 502–507, July 1991, Jones et al., Journal of Food Protection, Volume 54, No. 4, 259–262, April 1991). The intestinal contents of chickens may harbor up to $10^7$ Salmonella and/or Campylobacter per gram, and cross contamination during processing is frequent (Oosterom et al., Journal of Food Protection, Volume 46, No. 4, 339–344, April 1983). Studies have demonstrated that fecal material constitutes the major source from which edible parts of chickens are contaminated in processing plants. Therefore, to significantly reduce the level of contamination on processed poultry, pathogen-free or nearly pathogen-free birds must be delivered to the processing plant (Bailey, Poultry Science, Volume 72, 1169–1173, 1993).

Better control measures are needed to minimize the spread of these and other human enteropathogenic bacteria; and the most promising approach to achieve this end has been to decrease the incidence and level of colonization by these microorganisms in poultry gastrointestinal tracts. To date, the most effective means for controlling Salmonella colonization is competitive exclusion (CE). Although the exact mechanism of CE protection is unclear, it is likely to be influenced by factors such as pH, Eh, production of inhibitory substances such as $H_2S$, bacteriocins, fatty acids, and conjugated bile acids; competition for nutrients and receptor sites; and local immunity (Mead et al., Letters in Applied Microbiology, Volume 10, 221–227, 1990). Competitive exclusion treatment involves introduction of intestinal flora from pathogen-free adult birds into newly hatched chicks. A study by Nurmi et al. (Nature, Volume 241, 210–211, Jan. 19, 1973), first reported the use of the competitive exclusion technique. The reference discloses inoculation of 1 to 2 day old chicks by oral gavage with 1:10 dilution of normal intestinal flora and the birds were challenged with Salmonella. After 8–22 days, the birds were examined for the presence of Salmonella. It was found that only 33% of the treated birds were colonized with Salmonella whereas 100% of the untreated birds were colonized with Salmonella. Originally, a suspension of crop and intestinal tract materials from healthy, adult birds was used. In later studies, cecal content was cultured anaerobically in a liquid medium. It was found that preparations of subcultured intestinal contents from healthy, adult birds conferred protection to young chicks whose intestinal or gut microflora had not yet been established. Administration of undefined CE preparations to chicks speeds up the maturation of the gut flora in newly-hatched birds and also provides a substitute for the natural process of transmission of microflora from the adult hen to its offspring.

There are many competitive exclusion treatments related to the use of undefined mixtures of organisms obtained from cecal contents or cecal wall scrapings which are subcultured (Snoeyenbos et al., U.S. Pat. No. 4,335,107; Mikkola et al., U.S. Pat. No. 4,657,762; Stern et al., Avian Diseases, Volume 32,330–334, 1988; Stern, Poultry Science, Volume 75, 402–407, 1994; and Stern et al, U.S. patent applicaiton Ser. No. 08/031,983). While these undefined cultures have generally proven to be effective in reducing colonization of chickens with food borne pathogens, there are concerns regarding their safety since there is the possibility of transmission of etiological agents associated with human food borne disease and/or the transmission of avian disease.

U.S. patent application Ser. No. 08/282,580 (Line et al.), herein incorporated by reference in its entirety, discloses a defined CE preparation of yeast which reduces the populations of gram-negative enteropathogenic Campylobacter and Salmonella in poultry by administering the CE preparation by oral gavage, in drinking water, in feed, by spraying newly hatched chicks with an aqueous suspension, or a combination of the above. This treatment is most effective if administered as early as possible.

U.S. patent application Ser. No. 08/542,488 (Line et al.) herein incorporated by reference in its entirety, discloses the use of yeast as competitive exclusion microflora in ovo for the reduction of pathogen colonization.

Hafez et al. (Arch fur Geflugelkunde, Volume 59(1) :69–73, 1995) report treatment of hatching eggs, artificially infected with Salmonella enteritidis, with the quinolone, enrofloxacin, using pressure-differential-dipping. They found that for 10 minutes under reduced pressure in enrofloxacin, no S. enteritidis was reisolated from freshly hatched chicks. Using enrofloxacin at 5 minutes reduced pressure, they reisolated S. enteritidis from 2–4% of the new hatched chicks.

There are numerous potential sources of salmonellae contamination in a modern poultry operation, including chicks, feed, rodents, birds, insects, and the transportation and processing procedures to which the birds are subjected. These sources of contamination make it difficult to administer a competitive exclusion culture to a bird before it is first colonized by microorganisms such as Salmonella and Campylobacter. Therefore, there is a need in the art to introduce a competitive exclusion culture as early as possible to poultry.

There have been a number of reports of in ovo vaccination of avian embryos. In U.S. Pat. No. 5,206,015 (015), to Cox et al., a method is disclosed for introducing an aqueous preparation of unattenuated probiotic bacteria into the digestive tract of a bird to exclude undesirable bacteria from colonizing the digestive tract. The bacterial culture is administered by depositing it in the air cell (large end) of an egg. The digestive tract of the hatchling of the inoculated eggs is found to be colonized bythe bacterial culture at the time of hatch. In this method a hole is punched into the air cell end (large end) of the egg with a sterile needle, then the bacteria are administered using a smaller sterile needle, and finally the hole is either left unsealed or sealed with a bacteria-impermeable material.

U.S. Pat. No. 4,458,630 ('630) to Sharma et al. discloses an in ovo vaccination of avian eggs where the injection site is within either regions defined by the amnion or yolk sac. That is, the injection is midway along, and perpendicular to, the longitudinal axis for amnion penetration through the large end of the egg with a one inch needle so that the needle passes through the outer and inner shell membranes enclosing the air cell and amnion and terminates in the fluid above the chick or in the chick itself. As in '015 patent, a hole is punched or drilled in the shell and this may be resealed with parafilm or the like.

U.S. Pat. No. 4,040,388 ('388), to Miller teaches an automated method and apparatus for injecting embryonated eggs prior to incubation with a variety of substances into the albumin end (small end) of the egg. The reference teaches coagulative cooking of the surrounding albumin to seal the hole made by the injection. The drawbacks are that the vaccine is susceptible to inactivation during the heat coagulation step. Furthermore, Sharma et al. ('630) report that albumin has an inhibitory effect on the transport of an inoculant to the embryo at the egg's opposite end.

U.S. Pat. No. 2,851,006 ('006) to Taylor et al., teaches a method for increasing the hatch rate of bacterially infected eggs by means of in ovo treatment with a suitable bacteriophage in an aqueous preparation. The phage is introduced to the interior of the egg prior to incubation by any variety of techniques including by hypodermic syringe, pressure differential in a dipping fluid and jet spray. With the hypodermic syringe, a 26 gauge short shank needle is inserted at an oblique angle into the albumin end of the egg.

In U.S. Pat. No. 3,120,834 ('834), Goldhaft et al. expands the application taught in Taylor to a variety of substances including antibiotics, sulfonamides, vitamins, enzymes, nutrients, and inorganic salts. These agents are introduced through the shell prior to incubation by means of vacuum impregnation.

U.S. Patent No. 3,256,856 ('856) to Nicely et al. offers an improvement to the method of Goldhaft et al. in providing one or more holes in the egg shell for facilitating penetration. The hole(s) is (are) made in the air cell end (large end) of the egg, not extending beyond the inner shell membrane.

While there are various methods for in ovo introduction of microorganisms and other substances such as antibiotics, there still remains a need in the art for the earliest protection of poultry to reduce the populations of human enteropathogenic bacteria, such as for example, Campylobacter and Salmonella, in poultry. The present invention is different from prior art methods and provides for an in ovo method using a combination of a yeast preparation and an antibiotic.

SUMMARY OF THE INVENTION

It is therefore an object of the present invention to provide a method of in ovo treatment with a defined microbial preparation and an antibiotic to reduce or eliminate pathogen colonizatin in poultry.

Another object of the present invention is to provide a method of in ovo treatment with a yeast preparation and an antibiotic to reduce or eliminate pathogen colonization in poultry.

Another object of the present invention is to provide a method of in ovo treatment with a yeast preparation and quinolone antibiotic to reduce or eliminate pathogen colonization in poultry.

Further objects and advantages will become apparent from the following description.

DETAILED DESCRIPTION OF THE INVENTION

The importance of enteric infections in humans has been increasingly well recognized over the last dozen years. The relationship of poultry contamination and human infection has, likewise, become well documented. During broiler production and processing, fecal material containing pathogens are transferred onto meat and persist into food processing kitchens.

The application of a preparation of yeasts and antibiotics in ovo for the reduction and or prevention of pathogen colonization has been discovered. *S. cerevisiae* var. *boulardii* is a non-pathogenic yeast originally isolated growing on lychee fruit in Indochina in the 1920's (Surawicz et al., *Gastroenteroloqy*, Volume 96, 981–988, 1989). Since 1962 it has been used in several countries to treat antibiotic-associated diarrhea in humans. It has been used widely in Europe and is under study in the U.S. for treatment of patients whose intestinal microflora has been compromised by intensive antibiotic therapy (Surawicz et al., *American Journal of Gastroenterology*, Volume 84, 1285–1287, 1989; *Gastroenterology*, Volume 104, A786, 1993). Often in these patients, antibiotic resistant pathogens take advantage of the lack of competing organisms and colonize the intestines of the patients causing severe and sometimes fatal diarrhea. Administration of the protective *S. cerevisiae* var. *boulardii* prevents toxin formation by gram-positive *Clostridium difficile* until the patients' normal protective microflora can be restored (Buts et al., *Journal of Pediatric Gastroenteroloqy and Nutrition*, Volume 16, 419–425, 1993) and reduces the concentrations of several etiological agents of diarrhea (McFarland et al., *Microbial Ecoloqy in Health and Disease*, Volume 6, 157–171, 1993).

*S. cerevisiae* var. *boulardii* is rather thermophilic with an unusual optimum growth temperature of 37° C. It therefore is able to withstand the higher body temperature of poultry which is about 41.5° C. for chickens. The yeast has been shown to survive gastric acid in the stomach of mammals to reach the intestines (Bluehaut et al., *Biopharmaceutics and Drug Disposition*, Volume 10, 353–364, 1989), which indicates that it might survive passage through the crop, proventriculus, and gizzard of chickens to reach the intestines and ceca. It has demonstrated antagonistic activity in vitro and in vivo against various bacterial pathogens (Elmer et al., *Antimicrobial Agents and Chemotherapy*, 129–131, January 1987); and *S. cerevisiae* var. *boulardii can survive either aerobically or anaerobically, potentially making the culture and administration of the organism easier and more reliable than anaerobic cultures*.

Experimental evidence now strengthens the theory that the binding of bacteria to host cell-surface sugars initiates infection (Sharon et al., *Scientific American*, 82–89, January 1993). For example, *E. coli* have been demonstrated to exhibit a specific binding to the monosaccharide mannose. The host intestinal cells present mannose moieties which the *E. coli* attach to and initiate colonization of the intestines. Salmonella exhibit similar mannose-specific binding. The yeast, *S. cerevisiae* var. *boulardii*, contains high levels of mannose in its outer cell wall. It is believed that when the yeast is administered to chicks, the mannose presented by the yeast acts as a decoy to bind and agglutinate any Salmonella that may enter the gastrointestinal tract before the Salmonella can attach to the intestinal cell wall and initiate colonization of the bird. Since *S. boulardii* has been demonstrated not to permanently colonize poultry [unpublished data], the yeast and any yeast-bound Salmonella pass harmlessly out of the bird and Salmonella colonization is prevented.

The antibiotic chosen for practicing the present invention is not critical, and may be any of those conventionally employed for combatting bacterial infections in birds or active against human enteropathogenic bacteria. Preferred are antibiotics used for combatting Salmonella (e.g., *Salmonella typhimurium*) or *Escherichia coli* infections in birds, such as the aminoglycoside-aminocyclitols, the tetracyclines, the cephalosporins, and the quinolones. Quinolone antibiotics are preferred. Exemplary ceaphalosporins include, but are not limited to, Cephalothin, Cephapirin, Cefazolin, Cephalexin, Cephradine, Cefadroxil, Cefamandole, Cefoxitin, Cefaclor, Cefuorxime, Cefonicid, Ceforanide, Cefotaxime, Moxalactam, Ceftizoxime, Ceftriaxone, Cefoperazone, and Ceftiofur. Exemplary tetracyclines include, but are not limited to, Chlortetracycline, Oxytetracycline, Tetracycline, Demeclocycline, Methacycline, Doxycycline, and Minocycline. Exemplary aminoglycoside-aminocyclitol antibiotics include, but are not limited to KanamycinA, KanamycinB, KanamycinC, Tobramycin, DideoxykananmycinB, Amikacin, Gentamicin B, Gentamicin $C_{12}$, Gentamicin $C_l$, Sisomicin, Netilmicin, Neomycin, Paramomycin, Lividomycin, Ribostamycin, Butirosin, Streptomycin, Spectinomycin, and Apramycin. Exemplary quinolone antibiotics include, but are not limited to, Binfloxacin, Ciprofloxacin, Enrofloxacin, Norfloxacin, Pefloxacin, Amifloxacin, Pirfloxacin, Ofloxacin, Fleroxacin, Lemefloxacin, Danafloxacin, Difloxacin, Sarafloxacin, and Nalidixic Acid. A preferred quinolone antibiotic is enrofloxacin.

The antibiotic may be administered in any pharmaceutically acceptable carrier, such as a liquid solution. Aqueous carriers such as phosphate buffered saline are preferred.

The present invention may be practiced with any type of bird egg, including chicken, turkey, duck, goose, quail, ostrich or pheasant eggs. Chicken and turkey eggs are preferred, with chicken eggs most preferred. Eggs treated by the methods of the present invention are fertile eggs which are preferably in the fourth quarter of incubation. Chicken eggs are treated on about the fifteenth to eighteenth day of incubation (that is, the fifteenth to eighteenth day of embryonic development), and are most preferably treated on about the eighteenth day of incubation. Turkey eggs are preferably treated on about the twenty-first to twenty-sixth day of incubation, and are most preferably treated on about the twenty-fourth day of incubation.

The method of this invention is applicable to any avian animal whether domestic or wild and particularly to poultry that are raised for egg laying or for human consumption which could serve as carrier for target pathogens. Poultry includes all domestic fowl raised for eggs or meat and includes chickens, turkeys, geese, ducks, pheasants, and the like.

The target pathogens include all human enteropathogenic bacteria capable of colonizing poultry. Of particular interest are Salmonella. As used herein, "human enteropathogenic bacteria"are bacteria capable of or known to colonize the human alimentary canal, and which are capable of causing intestinal illness in a human host. Examples of human enteropathogenic bacteria include Salmonella species and *Escherichia coli*.

For the purposes of this invention, a yeast preparation refers to a microbial preparation wherein the microbes comprise, consist essentially of, or consist of yeast. As used herein, a defined yeast preparation is a microbial preparation wherein the microbes comprise, consist essentially of, or consist of known species of yeast. Yeast preparations may be monogeneric for yeast (i.e., contain a single strain of yeast) or polygeneric for yeast (i.e., contain more than one strain of yeast.

As used herein, undefined microbial cultures (or undefined microbial preparations) are suspensions or anaerobic cultures prepared from cecal or fecal materials obtained from healthy Salmonella-free adult birds; definitive bacterial or microbial profiles of these undefined microbial preparations remain elusive. Defined microbial cultures consist essentially of, or consist of, known microbes such as bacteria.

Defined microbial cultures and defined yeast preparations can be standardized and greatly lower the risk of transmission of human and/or avian pathogens. Lack of standardization and the possible transmission of human and/or avian pathogens that may be in the source materials from donor birds are concerns when using undefined microbial cultures.

Yeast includes any species and strains of Saccharomyces such as *S. cerevisiae* var *boulardii*, other *S. cerevisiae*, *S. Carlsbergensis*, *S. ellipsoideus*, *S. intermedius*, for example, and of particular interest is *Saccharomyces cerevisiae* var. *boulardii*. The yeast may be cultured or dried preparations may be used directly by dilution with a buffered solution, such as, for example, buffered peptone.

Avian eggs injected by the method of the present invention are fertile eggs which are preferably in the fourth quarter of incubation. Chicken eggs, for example, are treated on about the fifteenth to eighteenth day of incubation (the eighteenth day of embryonic development), and are most preferably treated on about the eighteenth day of incubation.

In methods according to the present invention, compositions are administered into arian eggs. As used herein, "administering"includes any suitable method of in ovo delivery as is known in the art. In ovo injection to deposit a composition in a pre-selected location within the egg using a needle, stylus or punch inserted through the egg shell is a preferred method of administration; a pilot hole may be formed in the egg shell prior to insertion of the needle or other device which delivers the composition being administered.

The site of administration of the microbial or yeast preparation in the avian egg may be within (1) the region defined by the amnion (including the amniotic fluid and the avian embryo), (2) the allantois (i.e., the allantoic sac), (3) the yolk sac or (4) the air cell. Preferably administration of the microbial or yeast preparation is within the air cell. The site of administration of the antibiotic in the avian egg may be within (1) the region define by the amnion (including the amniotic fluid and the avian embryo), (2) the allantois (i.e., the allantoic sac), (3) the yolk sac or (4) the air cell. Preferably administration of the antibiotic is within either the region defined by the amnion or within the allantois, and most preferably is within the region defined by the amnion.

The air cell is positioned at the large end of the egg adjacent the shell itself, and can be conveniently accessed by a shallow injection of yeast approximately about 5 mm into the amnion through the top of the large end of the egg. The antibiotic is injected using a deep injection (approximately 2.5 cm) into the amnion through the top of the large end of the egg. By the beginning of the fourth quarter of incubation, the amnion is sufficiently enlarged that penetration thereof is assured nearly all the time when the injection is made from the center of the large egg along the longitudinal axis.

The mechanism of injection is not critical, but it is preferred that the method not unduly damage the tissues and organs of the embryo or the extraembryonic membranes surrounding it so that treatment will not decrease hatch rate. A hypodermic syringe fitted with a needle of about No. 23 gauge is suitable. To inject into the air cell, the needle need only be inserted into the egg from just inside the inner surface of the egg to about five millimeters under the shell. A pilot hole may be punched or drilled through the shell prior to insertion of the needle so that the inoculator will not have to push hard, running the risk that the final thrust will go too deep or it will damage the shell and/or embryo. Furthermore, the pilot hole prevents damaging or dulling of the needle. If desired, the egg can be sealed with a substantially bacteria-impermeable sealing material such as wax or the like to prevent subsequent entry of undesirable bacteria.

It is envisioned that a high speed automated injection system for avian embryos will be particularly suitable for practicing the present invention. Numerous such devices are available, exemplary being those disclosed in U.S. Pat. Nos. 4,040,388, 4,469,047 and 4,593,646, all to Miller, and U.S. Pat. No. 5,176,101, as well as European Patent Application No. 87305746.7, the disclosures of which are incorporated herein by reference in their entirety. All such devices, as adapted for practicing the present invention, comprise egg holder means and an injector operatively connected to a reservoir or container containing an injection liquid comprising a defined microbial preparation or defined yeast preparation, and operatively connected to a second reservoir or container containing an injection liquid comprising an antibiotic. Alternatively, the injector may contain an injection liquid comprising both a defined microbial preparation (or defined yeast preparation) and an antibiotic. The injection is positioned to inject an egg carried by the egg holder means. Thus an apparatus of the present invention may comprise: egg holder means for retaining at least one egg, egg injector means containing a defined microbial or yeast preparation; and egg injector means containing an antibiotic; where the egg injector means are operatively associated with the egg holder means for injecting into each egg an amount of defined microbial or yeast preparation and an amount of antibiotic, the amount of defined microbial or yeast preparation and the amount of antibiotic effective in combination to reduce the human enteropathogenic bacteria contained in avians hatched from the injected egg, compared to that which would be expected without injection.

In the present methods, a microbial preparation (such as a yeast preparation) and an antibiotic are administered to an egg in amounts effective to reduce human enteropathogenic bacteria found in the gut of the hatchling obtained from the treated egg. As used herein, 'a reduction of bacteria' or 'reduced human enteropathogenic bacteria' refers to a reduction in numbers of bacteria compared to that which would be expected in a hatchling from an egg which did not receive treatment according to the methods of the present invention. Any accurate method of measuring, counting, and comparing bacteria present in the guts of hatchlings may be used for such comparisons, as would be apparent to those skilled in the art. As used herein, "in amounts effective", "an amount effective", or "an effective amount", refer to the amount of antibiotic administered and the amount of microbial preparation administered, wherein the effect of the combined administration acts to reduce human enteropathogenic bacteria found in hatchlings. Thus the amount of antibiotic may vary depending on the amount of microbial prepartion used, and vice versa.

In treating chicken eggs, microbial cultures or yeast preparations may be provided in doses of from about $10^4$, $10^6$, or $10^8$ microorganisms per egg to about $10^{10}$, $10^{12}$ or even $10^{14}$ microorganisms per egg. A preferred dose range of yeast preparation contains about $10^8$ to $10^{10}$ yeast per chicken egg, with a more preferred dose of $10^9$ yeast per chicken egg. These doses of microbial cultures or yeast preparations can be altered for use in larger eggs (e.g., ostrich) or smaller eggs (e.g., pheasant) as would be apparent to one skilled in the art. In treating chicken eggs, antibiotics may be provided in doses of from about 0.1 mg/egg to about 5.0 mg/egg, with a more preferred dose of 0.5 mg/egg. Doses may vary depending on the antibiotic used, and doses can be adjusted for use in eggs larger than, or smaller than, chicken eggs.

The methods of the present invention also provide embryonated avian eggs which contain a microbial preparation and an antibiotic, in amounts effective to reduce or eliminate colonization of newly hatched birds by human enteropathogenic bacteria. The microbial preparation is preferably a defined yeast preparation, and the microbial preparation and antibiotic are provided in amounts effective to prevent or reduce colonization of newly hatched birds by Salmonella.

As used herein, the terms "birds" or "avians" are intended to include males and females of any avian species, but is primarily intended to encompass poultry which are commercially raised for eggs or meat. Accordingly the term "bird" or "avian" is particularly intended to encompass hens, cocks and drakes of chickens, turkeys, ducks, geese, quail, ostriches, and pheasants. Chickens and turkeys are preferred.

The term "in ovo" as used herein refers to birds contained within an egg prior to hatch. Thus, the present invention may be conceived of as both a method of treating eggs as well as a method of treating a bird prior to hatch.

As used herein, incubating an avian egg to hatch refers to keeping a fertile or embryohated egg under conditions which allow the embryo to mature and hatch. As used herein a hatchling or newly hatched bird refers to a bird that has emerged from the egg within the past seven days.

The following examples are intended only to further illustrate the invention and are not intended to limit the scope of the invention as defined by the claims.

EXAMPLE 1

Preparation of the Yeast Composition

Yeast are prepared by growing and harvesting pure cultures of *Saccharomyces cerevisiae* var. *boulardii* using conventional microbiological culture, fermentation, and cell collection techniques well known to those of skill in the art.

*Saccharomyces cerevisiae* var. *boulardii* (s.b.) (formerly *S. boulardii*) [formerly ATCC #74012] has been redeposited under the Budapest Treaty as ATCC 74352 (American Type Culture Collection, 12301 Parklawn Drive, Rockville, Md. 20852-1776. It is propagated in liquid culture using Sabouraud dextrose broth (SDB, Difco, Detroit, Mich.) or any other suitable liquid mycological culture media. The yeast may also be grown on an agar surface using Sabouraud dextrose agar (SDA, Difco, Detroit, Mich.) or any other suitable mycological agar. Yeast grown in liquid culture medium is harvested by centrifugation and diluted in buffered peptone (BP) solution for delivery to the eggs. Yeast grown on agar surfaces may be harvested with a sterile cotton-tipped swab and diluted in BP solution for delivery to the eggs.

Alternatively, another strain *S. cerevisiae* var. *boulardii* obtained from Lallemand, Inc. has been deposited under the Budapest Treaty at the American Type Culture Collection (12301 Parklawn Drive, Rockville, Md. 20852-1776) as ATCC 74351. This is also available from Institut Pasteur, 25 Rue Du Docteur Roux, 75724 Paris CEDEX 15 France as Accession number CNCM-I-1079 deposited under the Budapest Treaty. This strain may also be purchased from Lallemand, Inc. as Levucell™ SB20, (1620 Préfontaine, Montréal, Québec, Canada H1W2N8). The SB20 yeast may be grown in a fermenter under simulated commercial conditions using sterilized molasses as the primary carbohydrate source or it may be directly used by dilution with a buffered solution, such as, for example, buffered peptone solution. The yeast population in liquid form is enumerated and found to contain approximately $10^{10}$ cfu/ml. It is stored at 4° C. until use.

EXAMPLE 2

In Ovo Treatment of chick embryos with yeast and/or enrofloxacin to reduce colonization of broiler chicks This experiment compares the in ovo treatment of broiler eggs with the yeast, *Saccharomyces boulardii* (Levucell™ SB20, approximately 20 billion CFU/gram, Lallemand Inc./

Agrimerica, Inc.) alone, to in ovo treatment with enrofloxacin (Baytril) alone, and Saccharomyces and enrofloxacin combined for reducing and/or preventing colonization with Salmonella.

240 broiler chicken eggs were purchased from a local hatchery on day 18 of incubation. The blunt ends of the eggs were swabbed with a 0.5% chlorine solution. The eggs were randomly divided into 8 groups of 30 eggs each. Duplicate treatment groups were assigned. A small (approximately 1 mm) hole was drilled in each egg. All eggs received a deep injection (approximately 2.5 cm) of either enrofloxacin or sterile water (approximately 0.1 ml) into the amnion followed by a shallow injection (approximately 0.5 cm) of either buffered peptone or *S. boulardii* (approximately $10^8$) into the air cell. Eggs treated with sterile water and peptone are positive control eggs. All injections were done using a 23 gauge needle. Following treatment, eggs were transferred into small table-top incubators maintained at 99.5° F. When at least 50% of the chicks were hatched, a mixture of 3 nalidixic acid resistant Salmonella strains (*S. tyhpimurium, S. montevideo*, and *S. californica*) was prepared and sprayed (between 8,000 and 16,000 cells in 10 ml buffered peptone) into each incubator (Table 1 below). The chicks remained in the hatching chamber environment for an additional period of time (See Table 1) before being moved by groups into 8 isolation units (1 $m^3$). The chicks were given a standard broiler starter ration and water ad libitum for one week. On day 7 post-hatch the chicks were sacrificed by cervical dislocation and the cecae from 10 birds in each group were aseptically removed and analyzed for Salmonella content. The cecae were diluted approximately 1:3 in buffered peptone and plated on BGS agar containing nalidixic acid for enumeration of Salmonella. The diluted cecae were incubated overnight at approximately 35° C. for recovery of injured or low numbers of Salmonella. These enriched samples were then analyzed for Salmonella content. The values are reported in Table 1 below and represent the percentage of samples found to be positive after enrichment.

The combination of *Saccharomyces boulardii* and *enrofloxacin* is more effective in all of these trials (12–17) than either substance alone. Also the yeast form (rehydrated dried yeast, fresh yeast, old liquid, frozen culture) may be important. The only trial in which yeast alone was effective in reducing Salmonella colonization was in Trial 13 which employed fresh liquid yeast culture. The yeast alone did not appear to be effective when it had been frozen in shipment to the labs (Trials 15–17).

EXAMPLE 3

Detail of Trial 13

The purpose of this experiment is to compare in ovo treatment of eggs with yeast (*S. boulardii*) alone, enrofloxacin (Baytril) alone or the combination of *Saccharomyces boulardii* and enrofloxacin, for reducing and/or preventing colonization of chicks with Salmonella.

TABLE 1

Summary of In Ovo Yeast/Baytril Trials

| Trial #: | 12 | 13 | 14 | 15 | 16 | 17 |
|---|---|---|---|---|---|---|
| Yeast/egg ($\times 10^8$): | Not Determined | 1.9 | 1.8 | 5.9 | 7.1 | 8.3 |
| Yeast Form: | rehydrated (1:4) | fresh liquid 2 weeks old | old liquid 6 weeks old | frozen | frozen | frozen |
| Salmonella Challenge (cfu Sal sprayed in incubator): | 8600 | 8100 | 7750 | 13950 | 15575 | 9750 |
| Exposure Time (h): | 12 | 12 | 12 | 12 | 26 | 5 |
| In Ovo Treatment Groups (% Salmonella Positive) | | | | | | |
| Control | 100 | 100 | 90 | 0 | 100 | 100 |
| Control | 100 | 90 | 0 | 100 | 100 | 100 |
| Sb | 100 | 0 | 100 | 10 | 100 | 100 |
| Sb | 100 | 20 | 100 | 100 | 100 | 50 |
| Baytril | 20 | 0 | 10 | 0 | 90 | 0 |
| Baytril | 100 | 100 | 0 | 60 | 0 | 0 |
| Sb + Baytril | 30 | 0 | 0 | 0 | 0 | 0 |
| Sb + Baytril | 10 | 0 | 0 | 0 | 0 | 0 |

Sb indicates administration of *S. boulardii* yeast preparation.

240 broiler chicken eggs were purchased from a local hatchery on day 18 of incubation. The blunt ends of the eggs were swabbed with a 0.5% chlorine solution. The eggs were randomly divided into 8 groups of 30 eggs each. Duplicate treatment groups were assigned (Table 2 below). A small (approximately 1 mm) hole was drilled in each egg. All eggs received a deep injection (approximately 2.5 cm) of either enrofloxacin or sterile water (approximately 0.1 ml) into the amnion followed by a shallow injection (approximately 0.5 cm) of either buffered peptone or *S. boulardii* (approximately $10^8$) into the air cell. Eggs treated with sterile water and peptone are positive control eggs. All injections were done using a 23 gauge needle. Following treatment, eggs were transferred into small table-top incubators maintained at 99.5° F. When at least 50% of the chicks were hatched, a mixture of 3 nalidixic acid resistant Salmonella strains (*S. tyhpimurium, S. montevideo*, and *S. california*) was prepared and sprayed (about 8,100 cells in 10 ml buffered peptone) into each incubator. The chicks remained in the hatching chamber environment for an additional twelve hours before being moved by groups into 8 isolation units (1 $m^3$). The chicks were given a standard broiler starter ration and water ad libitum for one week. On day 7 post-hatch the chicks were sacrificed by cervical dislocation and the cecae from 10 birds in each group were aseptically removed and analyzed for Salmonella content. The cecae were diluted approximately 1:3 in buffered peptone and plated on BGS agar containing nalidixic acid for enumeration of Salmonella. The diluted cecae were incubated overnight at approximately 35° C. for recovery of injured or low numbers of Salmonella. These enriched samples were then analyzed for Salmonella content. The values are reported in Table 2 below and represent the percentage of samples found to be positive after enrichment. The overall hatchability of all groups was 67.5%. This relatively low hatch was due, in part, to the fact that none of the eggs were candled prior to treatment. Hatchability was identical between all enrofloxacin-only and yeast-only treatment groups. Hatchability was highest in the groups receiving both Saccharomyces boulardii and enrofloxacin. The greatest reduction in percentage of chicks colonized with Salmonella was achieved in the groups treated with both Saccharomyces boulardii and enrofloxacin. The mean results from duplicate treatment groups demonstrated that, after sample enrichment, 95% of the positive control chicks were colonized with Salmonella; whereas, none of the chicks treated with both Saccharomyces boulardii and enrofloxacin were colonized. S. boulardii alone was also effective in reducing colonization. Only 10% of the chicks from groups treated with S. boulardii alone were positive for Salmonella. A mean of 50% of the chicks in the enrofloxacin-treated groups were colonized with Salmonella; however, colonization results were disparate between the duplicate groups. No Salmonella were recovered from the chicks in one of the enrofloxacin-treated groups; whereas, 100% of the chicks in the duplicate group were colonized at a high level. This Salmonella recrudescence phenomenon has been observed in enrofloxacin-treated chicks in a previous trial.

compared to that which would be expected without said administering steps.

2. The method of claim 1 wherein said avian egg is selected from the group consisting of chicken eggs, turkey eggs, geese eggs, duck eggs, pheasant eggs, and ostrich eggs.

3. The method of claim 1 wherein said defined microbial preparation and said antibiotic are administered to said egg by injection.

4. The method of claim 1 wherein said defined microbial preparation comprises yeast.

5. The method of claim 1 wherein said defined microbial preparation consists essentially of yeast.

6. The method of claim 1 wherein said defined microbial preparation consists of Saccharomyces selected from the group consisting of S. cerevisiae var. boulardii, S. cerevisiae, and mixtures thereof.

7. The method of claim 1 wherein said antibiotic is a quinolone antibiotic.

8. The method of claim 1 wherein said human enteropathogenic bacteria is Salmonella.

9. The method of claim 1 wherein said yeast preparation and said antibiotic are administered in amounts effective to essentially prevent Salmonella colonization of the gut of said avian egg's hatchling.

10. A method for treating avians in ovo comprising:
providing an avian egg containing a live embryonic bird;
administering a defined yeast preparation into the air cell of said avian egg;
administering a quinoline antibiotic to said avian egg in a region selected from the allantois and the region bounded by the amnion; and
incubating said avian egg to hatch, wherein the amount of human enteropathogenic bacteria contained in said avian egg's hatchling is reduced compared to that which would be expected without said administering steps.

TABLE 2

Hatchability and Salmonella colonization result following in ovo treatment.

| In Ovo Treatment Group Description | Deep (2.5 cm) Injection (amnion) | Shallow (0.5 cm) Injection (air cell) | Chicks Hatched (%) | Salmonella Positive Chicks (%) Before Enrichment | Salmonella Positive Chicks (%) After Enrichment | Mean Log Salmonella per gram ceca and contents |
|---|---|---|---|---|---|---|
| Pos Control | water | B. Peptone | 76.6 | 80 | 100 | 3.42 |
| Pos Control | water | B. Peptone | 56.6 | 80 | 90 | 2.91 |
| Sb | water | Sb | 63.3 | 0 | 0 | 0 |
| Sb | water | Sb | 63.3 | 10 | 20 | 0.87 |
| Baytril | Baytril | B. Peptone | 63.3 | 0 | 0 | 0 |
| Baytril | Baytril | B. Peptone | 63.3 | 100 | 100 | 6.38 |
| Sb + Baytril | Baytril | Sb | 73.3 | 0 | 0 | 0 |
| Sb + Baytril | Baytril | Sb | 80.0 | 0 | 0 | 0 |

The foregoing detailed description is for the purpose of illustration. Such detail is solely for that purpose and those skilled in the art can make variations therein without departing from the spirit and scope of the invention.

What is claimed is:

1. A method for treating avians in ovo comprising:
providing an avian egg containing a live embryonic bird;
administering a defined microbial preparation into the air cell of said avian egg;
administering an antibiotic to said avian egg in a region selected from the allantois and the region bounded by the amnion; and
incubating said arian egg to hatch,
wherein the amount of human enteropathogenic bacteria contained in said arian egg's hatchling is reduced 11. An egg injection apparatus comprising:
egg holder means for retaining at least one egg;
egg injector means containing a defined yeast preparation; and
egg injector means containing an antibiotic; said egg injector means operatively associated with said egg holder means for injecting into each said at least one egg an amount of said defined yeast preparation and an amount of said antibiotic, said amount of defined yeast preparation and said amount of antibiotic effective in combination to reduce the amount of human enteropathogenic bacteria contained in avians hatched from said at least one egg, compared to that which would be expected without said defined yeast preparation and said antibiotic.

* * * * *

UNITED STATES PATENT AND TRADEMARK OFFICE
CERTIFICATE OF CORRECTION

PATENT NO. : 5,722,342
DATED : March 3, 1998
INVENTOR(S) : J. Eric Line, Norman J. Stern, Nelson A. Cox, J. Stan Bailey, Catherine Ricks, Patricia Phelps and Michael Knight It is certified that error appears in the above-identified patent and that said Letters Patent is hereby corrected as shown below:

On title page, item [54] and column 1, lines 1-3 in

TITLE: IN OVO ANTIBIOTIC AND MICROBIAL TREATMENT TO

DIMINISH SALMONELLAE POPULATIONS IN AVIANS

Signed and Sealed this

Twenty-eighth Day of July, 1998

*Attest:*

BRUCE LEHMAN

*Attesting Officer*          Commissioner of Patents and Trademarks

UNITED STATES PATENT AND TRADEMARK OFFICE
CERTIFICATE OF CORRECTION

PATENT NO. : 5,722,342
DATED : March 3, 1998
INVENTOR(S) : J. Eric Line, et. al.

It is certified that error appears in the above-indentified patent and that said Letters Patent is hereby corrected as shown below:

Title page, item [73] should read as following:

Assignees: The United States of America, as represented by the Secretary of Agriculture
Washington, D.C.

Embrex, Inc.
1035 Swabia Court
Durham, North Carolina

Lallemand, Inc.
151 Skyway Ave., Rexdale
Ontario, Canada M9W 4Z5

Signed and Sealed this

Nineteenth Day of October, 1999

Q. TODD DICKINSON

*Attest:*

*Attesting Officer*        Acting Commissioner of Patents and Trademarks